(12) United States Patent
Ellingson et al.

(10) Patent No.: US 10,677,869 B2
(45) Date of Patent: Jun. 9, 2020

(54) PH-WEIGHTED MRI USING FAST AMINE CHEMICAL EXCHANGE SATURATION TRANSFER (CEST) IMAGING

(71) Applicant: The Regents of the University of California, Oakland, CA (US)

(72) Inventors: Benjamin Ellingson, Los Angeles, CA (US); Robert Harris, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 224 days.

(21) Appl. No.: 15/577,664

(22) PCT Filed: May 27, 2016

(86) PCT No.: PCT/US2016/034886
§ 371 (c)(1),
(2) Date: Nov. 28, 2017

(87) PCT Pub. No.: WO2016/196392
PCT Pub. Date: Dec. 8, 2016

(65) Prior Publication Data
US 2018/0164393 A1    Jun. 14, 2018

Related U.S. Application Data

(60) Provisional application No. 62/168,068, filed on May 29, 2015.

(51) Int. Cl.
*G01R 33/56* (2006.01)
*G01R 33/48* (2006.01)
(Continued)

(52) U.S. Cl.
CPC .......... *G01R 33/5605* (2013.01); *A61B 5/055* (2013.01); *G01N 24/08* (2013.01);
(Continued)

(58) Field of Classification Search
CPC .......... G01R 33/5605; G01R 33/56509; G01R 33/4838; G01R 33/5616; G01R 33/4616;
(Continued)

(56) References Cited

U.S. PATENT DOCUMENTS 5,339,035 A * 8/1994 Schneider ............ G01R 33/482
324/309
6,507,749 B1 * 1/2003 Macgowan .......... A61B 5/0263
324/307
(Continued)

FOREIGN PATENT DOCUMENTS

WO        2014165051 A1    10/2014

OTHER PUBLICATIONS

Castelli, D.D., Gianolio, E., Crich, S.G., Terreno, E. and Aime, S., 2008. Metal containing nanosized systems for MR-molecular imaging applications. Coordination Chemistry Reviews, 252(21-22), pp. 2424-2443. (Year: 2008).*

(Continued)

*Primary Examiner* — Christopher P McAndrew
(74) *Attorney, Agent, or Firm* — Quarles & Brady LLP

(57) ABSTRACT

A pH-weighted chemical exchange saturation transfer (CEST) magnetic resonance imaging (MRI) method and system are provided that works by indirectly measuring the NMR signal from amine protons found on the backbones of amino acids and other metabolites, which resonate at a frequency of +2.8-3.2 ppm with respect to bulk water protons. The technique uses a modified magnetization transfer radiofrequency saturation pulse for the generation of image contrast. A train of three 100 ms Gaussian pulses at high amplitude (6 uT) or Sinc3 pulses are played at a particular frequency off-resonance from bulk water prior to a fast echo planar imaging (EPI) readout, with one full image acquired at each offset frequency. This non-invasive (Continued)

pH-weighted MRI technique does not require exogenous contrast agents and can be used in preclinical investigations and clinical monitoring in patients with malignant glioma, stroke, and other ailments.

15 Claims, 7 Drawing Sheets

(51) Int. Cl.

| | |
|---|---|
| G01R 33/483 | (2006.01) |
| G01N 33/48 | (2006.01) |
| G01R 33/561 | (2006.01) |
| G01R 33/565 | (2006.01) |
| G01R 33/46 | (2006.01) |
| A61B 5/055 | (2006.01) |
| G01N 24/08 | (2006.01) |

(52) U.S. Cl.
CPC ......... *G01N 33/48* (2013.01); *G01R 33/4804* (2013.01); *G01R 33/4838* (2013.01); *G01R 33/4616* (2013.01); *G01R 33/5616* (2013.01); *G01R 33/56509* (2013.01); *G01R 33/56563* (2013.01)

(58) Field of Classification Search
CPC .......... G01R 33/56563; G01R 33/4804; G01N 33/48; G01N 24/08; A61B 5/055
USPC ........................................................ 324/309
See application file for complete search history.

(56) References Cited

U.S. PATENT DOCUMENTS

| | | | | |
|---|---|---|---|---|
| 7,941,204 | B1* | 5/2011 | Wang ................ | G01R 33/4824 600/420 |
| 8,278,925 | B2 | 10/2012 | Sun | |
| 2003/0160610 | A1* | 8/2003 | Van Zijl ............ | G01R 33/4804 324/300 |
| 2007/0088211 | A1* | 4/2007 | Cheng ................... | A61B 5/055 600/410 |
| 2008/0194944 | A1* | 8/2008 | Edelman ................ | A61B 5/055 600/420 |
| 2009/0315559 | A1 | 12/2009 | Herzka et al. | |
| 2010/0127703 | A1* | 5/2010 | Sung ..................... | A61B 5/055 324/309 |
| 2010/0142784 | A1 | 6/2010 | Yamykh | |
| 2010/0156413 | A1* | 6/2010 | Chen .................. | G01R 33/4828 324/307 |
| 2011/0181280 | A1 | 7/2011 | Weng | |
| 2012/0013336 | A1 | 1/2012 | Hetzer et al. | |
| 2013/0102879 | A1* | 4/2013 | Maclaren ............. | G01R 33/243 600/411 |
| 2013/0127460 | A1* | 5/2013 | Beck ...................... | G01N 24/08 324/309 |
| 2013/0190601 | A1* | 7/2013 | Alsop ................ | G01R 33/5601 600/410 |
| 2014/0070803 | A1* | 3/2014 | Jin ..................... | G01R 33/5605 324/309 |
| 2014/0300353 | A1* | 10/2014 | He ....................... | A61B 5/4312 324/309 |
| 2014/0333303 | A1* | 11/2014 | Paul ................. | G01R 33/34092 324/309 |
| 2015/0346304 | A1* | 12/2015 | Hu ........................ | A61B 5/055 600/411 |
| 2017/0285125 | A1* | 10/2017 | Daniel ............. | G01R 33/56509 |
| 2017/0328970 | A1* | 11/2017 | Bi ....................... | G01R 33/5619 |

OTHER PUBLICATIONS

Niitsu, M., Tohno, E. and Itai, Y., 2003. Fat suppression strategies in enhanced MR imaging of the breast: comparison of SPIR and water excitation sequences. Journal of Magnetic Resonance Imaging: An Official Journal of the International Society for Magnetic Resonance in Medicine, 18(3), pp. 310-314. (Year: 2003).*
Extended European search report issued in corresponding European Application No. 16804180.4, dated Jan. 3, 2019, 10 pages.
International Search Report and Written Opinion issued in corresponding International Application No. PCT/US2016/034886, dated Sep. 22, 2016, 12 pages.
Harris, Robert J. et al. "Simulation, phantom validation, and clinical evaluation of fast pH-weighted molecular imaging using amine chemical exchange saturation transfer echo planar imaging (CEST-EPI) in glioma at 3 T" NMR in Biomedicine, vol. 29, No. 11, Sep. 15, 2016, pp. 1563-1576, XP055527124, GB, ISSN: 0952-3480, DOI: 10.1002/nbm.3611.
Harris, Robert J. et al. "Simultaneous pH-sensitive and oxygen-sensitive MRI of human gliomas at 3 T using multi-echo amine proton chemical exchange saturation transfer spin-and-gradient echo echo-planar imaging (CEST-SAGE-EPI)" Magnetic Resonance in Medicine, vol. 80, No. 5, Apr. 6, 2018, pp. 1962-1978, XP055527132, US, ISSN:0740-3194, DOI: 10.1002/mrm.27204.
Sun, Phillip Zhe et al. "Investigation of Optimizing and Translating pH-Sensitive Pulsed-Chemical Exchange Saturation Transfer (CEST) Imaging to a 3T Clinical Scanner" Magnetic Resonance in Medicine, vol. 60, Sep. 24, 2008, pp. 834-841, XP002527196, DOI: 10 1002/MRM.21714.
Sun, Phillip Zhe et al. "Fast Multislice pH-Weighted Chemical Exchange Saturation Transfer (CEST) MRI With Unevenly Segmented RF Irradiation" Magnetic Resonance in Medicine, vol. 65, No. 2, Sep. 24, 2010, pp. 588-594, XP055159498, ISSN: 0740-3194, DOI: 10.1002/mrm.22628.
Zhu, He et al. "Fast 3D Chemical Exchange Saturation Transfer (CEST)Imaging of the Human Brain" Magnetic Resonance in Medicine, vol. 64, No. 3, Jul. 14, 2010, pp. 638-644, XP055027751, ISSN: 0740-3194, DOI: 10.1002/mrm.22546.
Boxerman JL, et al. Relative cerebral blood volume maps corrected for contrast agent extravasation significantly correlate with glioma tumor grade, whereas uncorrected maps do not AJNR Am J Neuroradiol. 2006;27(4):859-867.
Cai K, et al. Magnetic resonance imaging of glutamate. Nat Med. 2012;18(2):302-306.
Cai K, et al. Mapping glutamate in subcortical brain structures using high-resolution GluCEST MRI. NMR Biomed. 2013;26(10):1278-1284.
Freeman ML, et al. An acidic extracellular environment reduces the fixation of radiation damage. Radiat Res. 1984;97(1):154-161.
Gatenby RA, et al. Why do cancers have high aerobic glycolysis? Nat Rev Cancer. 2004;4(11):891-899.
Griffiths L, et al. The influence of oxygen tension and pH on the expression of platelet-derived endothelial cell growth factor/thymidine phosphorylase in human breast tumor cells grown in vitro and in vivo. Cancer Res. 1997;57(4):570-572.
Harris, Robert J., et al. "pH-weighted molecular imaging of gliomas using amine chemical exchange saturation transfer MRI." Neuro-oncology 17.11 (2015): 1514-1524.
Helmlinger G, et al. Acid production in glycolysis-impaired tumors provides new insights into tumor metabolism. Clin Cancer Res. 2002;8(4):1284-1291.
Jin T, et al. Magnetic resonance imaging of the amine-proton exchange (APEX) dependent contrast. Neuroimage. 2012;59(2):1218-1227.
Jones CK, et al. Nuclear Overhauser enhancement (NOE) imaging in the human brain at 7T. Neuroimage. 2013;77:114-124.
Kim M, et al. Water saturation shift referencing (WASSR) for chemical exchange saturation transfer (CEST) experiments. Magn. Reson Med. 2009;61(6):1441-1450.
Kinahan PE, et al. Attenuation correction for a combined 3D PET/CT scanner. Med Phys. 1998;25(10):2046-2053.
Kogan F, et al. Imaging of glutamate in the spinal cord using GluCEST. Neuroimage. 2013;77:262-267.
Kovacevic Z, et al. The role of glutamine in the oxidative metabolism of malignant cells. Cancer Res. 1972;32(2):326-333.

(56) References Cited

OTHER PUBLICATIONS

Lardner A. The effects of extracellular pH on immune function. J Leukoc Biol. 2001;69(4):522-530.
Martinez-Zaguilan R, et al. Acidic pH enhances the invasive behavior of human melanoma cells. Clin Exp Metastasis. 1996;14(2):176-186.
McConnell HM. Reaction rates by nuclear magnetic resonance. J Chem Phys. 1958;28(3):430-431.
McMahon MT, et al. Quantifying exchange rates in chemical exchange saturation transfer agents using the saturation time and saturation power dependencies of the magnetization transfer effect on the magnetic resonance imaging signal (QUEST and QUESP): pH calibration for poly-L-lysine and a starburst dendrimer. Magn Reson Med. 2006;55(4):836-847.
McVicar N, et al. Quantitative tissue pH measurement during cerebral ischemia using amine and amide concentration-independent detection (AACID) with MRI. J Cereb Blood Flow Metab. 2014;34(4):690-698.
Medina MA, et al. Relevance of glutamine metabolism to tumor cell growth. Mol Cell Biochem. 1992;113(1):1-15.
Morita T, et al. Clastogenicity of low pH to various cultured mammalian cells. Mutat Res. 1992;268(2):297-305.
Nuyts J, et al. Maximum-likelihood expectation-maximization reconstruction of sinograms with arbitrary noise distribution using NEC-transformations. IEEE Trans Med Imaging. 2001;20(5):365-375.
Paech D, et al. Nuclear overhauser enhancement mediated chemical exchange saturation transfer imaging at 7 Tesla in glioblastoma patients. PLoS One. 2014;9(8):e104181.
Perry TL, et al. Free amino acids and related compounds in biopsies of human brain. J Neurochem. 1971;18(3):521-528.
Raghunand N, et al. Microenvironmental and cellular consequences of altered blood flow in tumours. Br J Radiol. 2003;76 Spec No. 1:S11-S22.
Reichert M, et al. Modulation of growth and radiochemosensitivity of human malignant glioma cells by acidosis. Cancer. 2002;95(5):1113-1119.
Schmainda KM, et al. Characterization of a first-pass gradient-echo spin-echo method to predict brain tumor grade and angiogenesis. AJNR Am J Neuroradiol. 2004;25(9):1524-1532.
Schmitt B, et al. Optimization of pulse train presaturation for CEST imaging in clinical scanners. Magn Reson Med. 2011:65(6):1620-1629.
Shi Q, et al. Regulation of vascular endothelial growth factor expression by acidosis in human cancer cells. Oncogene. 2001;20(28):3751-3756.
Souba WW. Glutamine and cancer. Ann Surg. 1993;218(6):715-728.
Sun PZ, et al. Early experience of translating pH-weighted MRI to image human subjects at 3 Tesla. Stroke. 2010;41(10 Suppl):S147-S151.
Togao O, et al. Amide proton transfer imaging of adult diffuse gliomas: correlation with histopathological grades. Neuro Oncol. 2014;16(3):441-448.
Wachsberger P, et al. Tumor response to ionizing radiation combined with antiangiogenesis or vascular targeting agents: exploring mechanisms of interaction. Clin Cancer Res. 2003;9(6):1957-1971.
Wen PY, et al. Updated response assessment criteria for high-grade gliomas: response assessment in neuro-oncology working group. J Clin Oncol. 2010;28(11):1963-1972.
Xu J, et al. On the origins of chemical exchange saturation transfer (CEST) contrast in tumors at 9.4T. NMR Biomed. 2014;27(4):406-416.
Zaiss M, et al. Relaxation-compensated CEST-MRI of the human brain at 7T: unbiased insight into NOE and amide signal changes in human glioblastoma. Neuroimage. 2015;112:180-188.
Zhou J, et al. Differentiation between glioma and radiation necrosis using molecular magnetic resonance imaging of endogenous proteins and peptides. Nat Med. 2011;17(1):130-134.
Zong, Xiaopeng, et al. "Sensitivity and source of amine-proton exchange and amide-proton transfer magnetic resonance imaging in cerebral ischemia." Magnetic resonance in medicine 71.1 (2014): 118-132.

* cited by examiner

PH-WEIGHTED MRI USING FAST AMINE CHEMICAL EXCHANGE SATURATION TRANSFER (CEST) IMAGING

CROSS-REFERENCE TO RELATED APPLICATIONS

This application represents the national stage entry of PCT International Application PCT/US2016/034886 filed May 27, 2016 and claims priority to U.S. Provisional Patent Application 62/168,068 filed on May 29, 2015. The contents of this application are hereby incorporated by reference as if set forth in their entirety herein.

STATEMENT REGARDING FEDERALLY SPONSORED RESEARCH OR DEVELOPMENT

This invention was made with Government support under CA167354, awarded by the National Institutes of Health. The Government has certain rights in the invention.

INCORPORATION-BY-REFERENCE OF COMPUTER PROGRAM APPENDIX

Not Applicable

BACKGROUND

1. Technical Field

The present technology pertains generally to medical imaging methods, and more particularly to methods for pH-weighted magnetic resonance imaging using amine chemical exchange saturation transfer echo planar imaging (CEST-EPI).

2. Background Discussion

Pronounced changes in tissue pH may be observed with numerous injurious conditions in humans, including cancer growth, stroke hypoxia, and seizure activity such as epilepsy. For example, it has been observed that tissue acidosis contributes directly to a microenvironment that is hospitable to many cancers. Various studies have reported that tumor cells have alkaline intracellular pH values (7.1-7.6 compared with 7-7.2 in normal tissues) and acidic extracellular pH values (6.2-6.9 compared with 7.3-7.4 in normal tissues). This decrease in extracellular pH is thought to be directly due to tumor size and altered blood flow, leading to increased hypoxia. This lack of oxygen increases glycolysis resulting in the accumulation of carboxylic acid and/or lactic acid in the extracellular spaces. Additionally, active transport of protons out of tumor cells to maintain high intracellular pH results in further decreases in pH within the immediate environment. These effects are further exacerbated by a diminished buffering capability of tumor interstitial fluid along with limited elimination of lactic acid and protons into the blood vasculature.

The increase in extracellular acidity comes with dramatic consequences, as it can be directly linked to the degree of tumor aggressiveness. In particular, a decrease in extracellular pH can result in decreased immune function, increased chromosomal rearrangements, increased tumor invasion, and increased angiogenesis through elevated VEGF and platelet-derived endothelial cell growth factor.

The decrease in extracellular pH also results in resistance to various forms of therapy including resistance to radiation therapy and specific chemotherapies. Thus, a non-invasive imaging method for spatially identifying regions of low tissue pH may be invaluable for early identification of malignant transformation, predicting early treatment resistance, as well as potentially detecting early tumor invasion, proliferation, angiogenesis, hypoxia, genetic mutations, and altered immune response.

Some positron emission tomography (PET) imaging techniques have shown sensitivity to pH, but this requires the use of an exogenous radiotracer. Similarly, some paramagnetic CEST contrast agents can be sensitive to pH, but this also requires the use of exogenous agents that are not currently FDA approved for humans.

Accordingly, there is a need for the development methods for non-invasively measuring altered, typically decreased, tissue pH in patients that does not require the use of exogenous contrast agents. There is also a need for fast, high spatial resolution pH imaging techniques for clinical evaluation of cancers, including gliomas. The present technology satisfies these needs.

BRIEF SUMMARY

The present technology provides a pH-weighted chemical exchange saturation transfer (CEST) magnetic resonance imaging (MRI) technique that works by indirectly measuring the NMR signal from amine protons found on the backbones of amino acids and other similar metabolites, which resonate at a frequency of +2.8-3.2 ppm with respect to bulk water protons. Chemical exchange saturation transfer (CEST) is a magnetic resonance imaging (MRI) technique that generates image contrast dependent on the chemical exchange between water protons and labile protons on various other molecules, including macromolecules and smaller metabolites. By selectively applying preparatory radiofrequency (RF) pulses to saturate the longitudinal magnetization of proton species found on molecules undergoing active chemical exchange with bulk water prior to standard acquisition of the MR signal at the water proton resonance, the resulting CEST image is attenuated to a degree that is dependent upon the concentration of labile protons and their chemical exchange rate, which in turn is dependent on temperature and pH. Thus, CEST imaging allows for estimation of both the concentration of specific molecular species as well as important physiologic parameters including pH.

The method targets the amine protons on glutamine and other amino acids for chemical exchange saturation transfer (CEST) imaging. It has been observed that the concentration of mobile glutamine and other neutral amino acids are elevated in regions of active tumor because they are a major source of fuel for malignant tumors and tumor transport systems are often amplified to increase glutamine consumption.

Since glutamine contains an amine and an amide group having different chemical shift frequencies (2.8-3.0 ppm and 3.5 ppm, respectively), compared to water protons, the method provides a higher CEST contrast at 2.8-3.0 ppm and glutamine can be used as an imaging biomarker for mapping regions of low pH which may be specific to viable tumor microenvironments.

The elevated levels of amino acids in areas of active tumor serve to amplify, rather than dilute, the CEST contrast in regions of low pH. In the current study we demonstrate that the amine proton CEST signal increases with increasing amino acid concentration and decreasing pH, and that this pH-weighted molecular MRI technique can be used to provide new insight into brain tumor physiology and behavior beyond traditional structural and functional imaging technologies.

Some previous studies have reported pH-weighted contrast from amide proton transfer (APT) imaging, a form of CEST imaging that targets protons on the backbones of proteins at approximately 3.5ppm frequency offset from water protons. The present technique differs from APT imaging in two important ways. First, studies have shown that the pH-weighted contrast decreases with decreasing pH for APT, meaning that more acidic (pathologic) tissue would show negative contrast on these images in the form of signal voids, which is not desirable and can be misinterpreted and are prone to image artifacts. Second, APT imaging requires a saturation preparation pulse on the order of seconds in length, typically ~3 s, to generate contrast. The present technique is targeted to the fast-exchanging amine protons and only requires RF saturation preparation on the order of 300 ms, at high amplitude. As the preparation pulse comprises the longest part of the image acquisition, this allows a dramatic reduction in scan time and the acquisition of more image slices or more averages, improving image quality.

The technique preferably utilizes a modified magnetization transfer (MT) radiofrequency (RF) saturation pulse for generation of image contrast. A train of three 100 ms Gaussian pulses at high amplitude (6 µT) are played at a particular frequency off-resonance from bulk water prior to a fast readout such as echo planar imaging (EPI), with one full image acquired at each offset frequency. At the beginning of the EPI readout, a 1-2-1 water-only RF excitation pulse is employed to avoid influence of chemical shift from fat protons. A total of 29 images are acquired at off-resonance saturation frequencies of +/−0, 0.1, 0.2, 0.3, 2.5, 2.6, 2.7, 2.8, 2.9, 3.0, 3.1, 3.2, 3.3, 3.4, and 3.5 ppm. A reference "$S_0$" image is also acquired using the same imaging parameters with no MT pulse. Data is then motion corrected and corrected for $B_0$ inhomogeneity. The asymmetry around 2.8-3.2 ppm is then calculated for each voxel by taking the integral of −2.8, −2.9, −3.0, −3.1, and −3.2 ppm, subtracting the integral of 2.8, 2.9, 3.0, 3.1, and 3.2 ppm, and dividing by the signal intensity of the $S_0$ image, in one embodiment. These asymmetry images are pH-weighted, showing increasing positive contrast with decreasing pH within a physiologically relevant range (~6.2-7.2 pH units). This technique does not require exogenous contrast agents and can be implemented for use in clinical monitoring of patients with glioma, stroke, and other ailments.

According to one aspect of the technology, a pH-weighted chemical exchange saturation transfer (CEST) magnetic resonance imaging (MRI) technique is provided that works by indirectly measuring the NMR signal from amine protons.

Another aspect of the technology is to provide a system that provides high resolution, pH-weighted imaging of the tissue microenvironment without the use of exogenous compounds or radioactivity.

A further aspect of the technology is to provide an imaging system and methods that uses high-amplitude RF pulses with short RF saturation pulse times that dramatically reduce scan times so that more image slices or more averages can be acquired per scan, greatly improving image quality.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 1 is a pulse sequence diagram for fast chemical exchange saturation transfer echo planar imaging (CEST-EPI) through one repetition. $t_0$ represents the start of the saturation pulse train, which ends at $t_1$. Spoiling gradients are played between $t_1$ and $t_2$. The spatial-spectral water-only excitation RF pulse is applied between $t_2$ and $t_3$. Between $t_3$ and $t_4$, EPI readout occurs. The time between $t_4$ and $t_5$ represents the time between the completion of readout and the start of the next repetition, which increases with TR. $t_5$ is equivalent to $t_0$ for the subsequent repetition.

DETAILED DESCRIPTION

Figure 1:
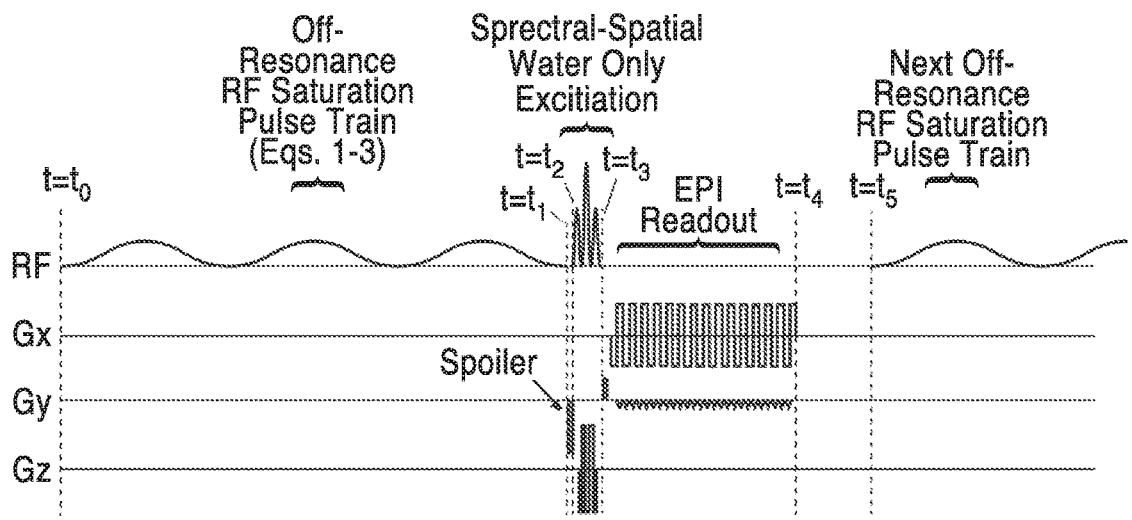

Referring more specifically to the drawings, for illustrative purposes, embodiments of the imaging system and methods are generally shown. Several embodiments of the technology are described generally in FIG. 1 through FIG. 7C to illustrate the systems and methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Chemical exchange saturation transfer (CEST) MRI targeting fast exchanging amine protons can be used to obtain high resolution pH-weighted images with a CEST echoplanar imaging (EPI) pulse sequence. The pH-weighted CEST magnetic resonance imaging technique works by indirectly measuring the NMR signal from amine protons found on the backbones of amino acids and other similar metabolites, which resonate at a characteristic range of frequencies with respect to bulk water protons.

The methods utilize a two-pool model of bulk water and fast-exchanging amine protons, with modifications to account for various RF saturation pulse characteristics and clinical imaging factors specific to the CEST echo planar imaging (EPI) sequence for fast clinical pH-weighted imaging.

The magnetization of bulk water protons undergoing two-pool chemical exchange with labile proton groups can be described by the Bloch-McConnell equations in the form of:

$$\frac{dM(t)}{dt} = X \cdot M(t) - c; \text{ where}$$

$$M = \begin{pmatrix} M_{ax} \\ M_{bx} \\ M_{ay} \\ M_{by} \\ M_{az} \\ M_{bz} \end{pmatrix}, X = \begin{pmatrix} C_{2a} & k_b & -\delta a & 0 & 0 & 0 \\ k_a & C_{2b} & 0 & -\delta b & 0 & 0 \\ \delta a & 0 & C_{2a} & k_b & -\omega_1 & 0 \\ 0 & \delta b & k_a & C_{2b} & 0 & -\omega_1 \\ 0 & 0 & \omega_1 & 0 & C_{1a} & k_b \\ 0 & 0 & 0 & \omega_1 & k_a & C_{1b} \end{pmatrix},$$

$$c = \begin{pmatrix} 0 \\ 0 \\ 0 \\ 0 \\ M_{az0}/T_{1a} \\ M_{bz0}/T_{1b} \end{pmatrix};$$

where pool A and pool B are the bulk water protons and labile protons, respectively; where $M_{az0}$ and $M_{bz0}$ are the equilibrium magnetizations of pool A and B, respectively; where $k_b$ is the exchange rate of protons from pool B to pool A; where $k_a$ is the exchange rate of protons from pool A to pool B as given by $(M_{b0}/M_{a0}) \cdot k_b$; where $\omega_1$ is the RF pulse amplitude as given by $\omega_1 = \gamma B_1(t)$, where $\gamma$ is the gyromagnetic ratio and $B_1(t)$ is given in $\mu T$; where $\delta a = \omega - \omega_a$ and $\delta b = \omega - \omega_b$; where $\omega$ is the applied RF irradiation frequency, $\omega_a$ is the bulk water resonance frequency, and $\omega_b$ is the labile proton irradiation frequency; where $T_{1a}$ and $T_{1b}$ are the longitudinal relaxation times of pool A and B, respectively; and where $C_{1a}=(1/T_{1a})+k_a$, $C_{2a}=(1/T_{2a})+k_a$, $C_{1b}=(1/T_{1b})+k_b$, $C_{2b}=(1/T_{2b})+k_b$ represent the sum of exchange and relaxation rates.

The Bloch-McConnell equations can be solved analytically to yield:

$$M(t)=e^{Xt} \cdot M_0(X/c)-(X/c)$$

where $M_{az}(t_1)$ represents the longitudinal magnetization of bulk water available for subsequent readout after CEST effects as illustrated in FIG. 1. Assuming the spoiler duration $(t_2-t_1)$ and water excitation pulse duration $(t_3-t_2)$ are negligible, $M_{az}(t_1)=M_{az}(t_3)$ reflects the available longitudinal magnetization for subsequent readout.

During CEST imaging, the RF saturation frequency $\omega$ may be swept across a range of values to obtain a spectral dataset called a "z-spectrum". To reduce the effects of $T_1$ and $T_2$ weighting along with other variables, the attenuation of bulk water magnetization following a saturation pulse is often described by the magnetization transfer ratio (MTR), given by:

$$MTR(\omega) = \frac{S(\omega)}{S_0}$$

where $S(\omega)$ is the amount of bulk water signal available after the saturation pulse with frequency $\omega$ and $S_0$ is the signal available without application of RF saturation. Since MTR can be affected by symmetric effects of direct water saturation and conventional magnetization transfer (MT) effects, CEST contrast is described by the asymmetry in the magnetization transfer ratio ($MTR_{asym}$) with respect to water proton resonance:

$$MTR_{asym}(\omega) = \frac{S(-\omega) - S(\omega)}{S_0}$$

Additionally, implementation of CEST imaging in a clinical environment often requires the acquisition of multiple slices and offset frequencies combined with a short TR for reduced scan time. Also, the use of non-selective saturation of the metabolite pool combined with a short TR may result in steady-state saturation after several pulses, which can change the amount of available CEST contrast to accurately estimate the longitudinal magnetization available for subsequent image acquisition. This relaxation is described by the Bloch-McConnell equations under the condition $B_1=0$, which for the longitudinal magnetization simplifies to:

$$M_{az}(t_5) = M_{az0} - [M_{az0} - M_{az}(t_1)] * e^{-\frac{t_5-t_1}{T_{1a}}}$$

$$M_{bz}(t_5) = M_{bz0} - [M_{bz0} - M_{bz}(t_1)] * e^{-\frac{t_5-t_1}{T_{1b}}}$$

where $M_{az}(t_1)$ is the longitudinal magnetization of water protons and $M_{bz}(t_1)$ is the longitudinal magnetization of metabolite protons following completion of the current off-resonance RF saturation pulse train; where $M_{az}(t_5)$ and $M_{bz}(t_5)$ are the longitudinal magnetization for the water and metabolite protons available just prior to the next off-resonance saturation pulse train; where $t_5-t_1$ is the time between subsequent off-resonance RF saturation pulse trains; and where $T_{1a}$ and $T_{1b}$ are the longitudinal relaxation times for the water and metabolite protons, respectively. CEST sequences often utilize spoiling gradients to destroy remaining transverse magnetization between off-resonance RF saturation and acquisition of the bulk water signal (i.e. from $t_1$ to $t_2$). Therefore, to account for the effects of spoiling gradients, transverse magnetization components were set to zero following each saturation pulse.

Lastly, the effects of pH on the CEST signal were modeled by accounting for the chemical exchange rate between protons on bulk water and metabolites. The chemical exchange between amino acid amine protons and protons in bulk water can be characterized as a base-catalyzed process, governed by the equation:

$$k_b = k_0 + k_{base} * 10^{-(14-pH)}$$

where $k_0$ is the default exchange rate, $k_{base}$ is the base-catalyzed rate constant, and $k_b$ is the exchange rate of protons from the metabolite proton pool to the water pool.

Figure 2A:
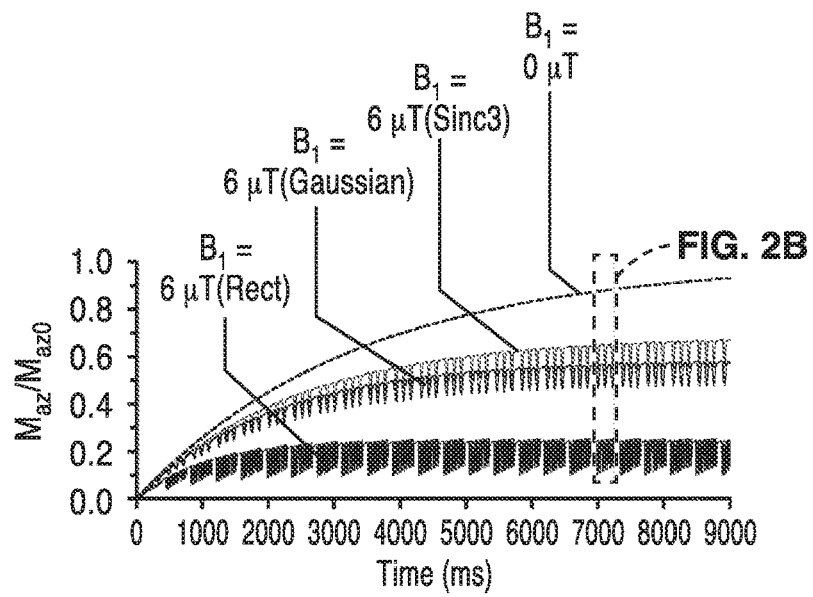
FIG. 2A is a graph of simulated longitudinal bulk water magnetization ($M_{az}$) at 3.0ppm during CEST-EPI acquisition in a sample of glutamine in water at pH=6.0.
Figure 2B:
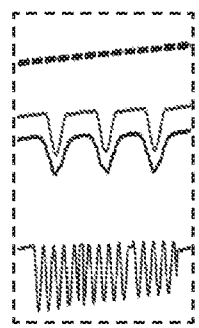
FIG. 2B is a detail view of the graph of FIG. 2A showing the $M_{az}$ evolution for rectangular, Gaussian and Sinc3 saturation pulses.

Turning now to FIG. 1 and FIG. 2, one preferred embodiment of a pulse sequence diagram for fast chemical exchange saturation transfer echo planar imaging (CEST-EPI) through one repetition and a pulse train are illustrated. Initially, the technique relies on a modified magnetization transfer (MT) radiofrequency (RF) saturation pulse for the generation of image contrast. In the embodiment of the method that is shown in FIG. 1 and FIG. 2, the imaging has the following steps:

(1) a train of three 100 ms Gaussian pulses at high amplitude (6 μT) or Sinc3 pulses are played at a particular frequency off-resonance from bulk water prior to a fast readout such as an echo planar imaging (EPI) readout, with one full image acquired at each offset frequency.

(2) Optionally a spoiler gradient can be applied to minimize transverse magnetization.

(3) At the beginning of the EPI readout, a 1-2-1 water-only RF excitation pulse is employed to avoid influence of chemical shift from fat protons. For example, a total of 29 images may be acquired at off-resonance saturation frequencies of +/−0, 0.1, 0.2, 0.3, 2.5, 2.6, 2.7, 2.8, 2.9, 3.0, 3.1, 3.2, 3.3, 3.4, and 3.5 ppm.

(4) Then a reference "$S_0$" image can also be acquired using the same imaging parameters with no MT pulse.

(5) Optionally, the acquired data may then be motion corrected and corrected for $B_0$ inhomogeneity.

(6) The asymmetry around 2.8-3.2 ppm is then calculated for each voxel by taking the integral of −2.8, −2.9, −3.0, −3.1, and −3.2 ppm, subtracting the integral of 2.8, 2.9, 3.0, 3.1, and 3.2 ppm, and dividing by the signal intensity of the $S_0$ image.

The acquired asymmetry images are pH-weighted, showing increasing positive contrast with decreasing pH within a physiologically relevant range (~6.2-7.2 pH units). This technique does not require exogenous contrast agents and is non-invasive. It can also be used in pre-clinical investigations and clinical monitoring in patients with malignant glioma, stroke, and other ailments.

The methods are implemented on a MRI scanner system with an imaging controller with a computer processor coupled to the imaging scanner and a non-transitory computer-readable memory storing instructions executable by the computer processor. Control over the scanner operation and imaging are provided by the controller computer and software.

The technology described herein may be better understood with reference to the accompanying examples, which are intended for purposes of illustration only and should not be construed as in any sense limiting the scope of the present technology described herein as defined in the claims appended hereto.

EXAMPLE 1

To demonstrate that chemical exchange saturation transfer (CEST) MRI can be used as a non-invasive pH-weighted molecular imaging technique by targeting the chemical exchange between amine protons and protons in extracellular bulk water, simulations of amine CEST contrast specific for the CEST echoplanar imaging (EPI) pulse sequences were performed. The accuracy of the simulations was validated by comparing the exchange rates and z-spectrum under a variety of conditions using physical phantoms of glutamine with different pH.

An analytical solution for CEST contrast using the two-pool model of bulk water and fast-exchanging amine protons was used with modifications to account for various RF saturation pulse characteristics and clinical imaging factors specific to the CEST echo planar imaging (EPI) sequence for fast clinical pH-weighted imaging. The properties of the RF saturation pulse were modulated including pulse shape, amplitude, and pulse train length, as well as clinical acquisition parameters and the simulations were verified using CEST-EPI applied to physical phantoms containing amino acids at known pH.

An illustration of a pulse sequence for fast chemical exchange saturation transfer echo planar imaging (CEST-EPI) through one repetition is shown in FIG. 1. The saturation pulse train starts at $t_0$ and ends at $t_1$. Spoiling gradients are played between $t_1$ and $t_2$. The spatial-spectral water-only excitation RF pulse is applied between $t_2$ and $t_3$. Between $t_3$ and $t_4$, EPI readout occurs. The time between $t_4$ and $t_5$ represents the time between the completion of readout and the start of the next repetition, which increases with TR. In addition, $t_5$ is equivalent to $t_0$ for the subsequent repetition.

Because the bulk water longitudinal magnetization in a particular slice is set approximately equal to zero during readout by the 90° spectral-spatial water only excitation pulse illustrated in FIG. 1, the $M_{az0}$ was set equal to zero at the start of each simulation. The amount of longitudinal magnetization available in the same slice during the next readout is dependent upon the properties of saturation and recovery that occur during the intervening period. Typically, a total of 25 slices were assumed in the simulation using a minimum TR. This number of slices is appropriate for achieving full brain coverage (~100 mm) with a reasonable slice thickness (4 mm). The minimum TR was chosen as the default to minimize total scan time, which is clinically desired.

The saturation pulse train consisted of three pulses of amplitude $B_1 = 6$ μT that was implemented using a Gaussian, Sinc3, or a rectangular waveform. To correct for $S_0$ as described in $$MTR(\omega) = \frac{S(\omega)}{S_0} \text{ and } MTR_{asym}(\omega) = \frac{S(-\omega) - S(\omega)}{S_0},$$

each simulation was followed by the application of an identical simulation with $B_1 = 0$ μT. The longitudinal magnetization at readout was taken as the value of $S_0$, and MTR or $MTR_{asym}$ were calculated accordingly.

For example, longitudinal bulk water magnetization ($M_{az}$) at 3.0ppm during CEST-EPI acquisition in a sample of glutamine in water at pH=6.0 was simulated as shown in FIG. 2. Scan parameters were TR=380 ms, number of slices=25, pulse length=100 ms, pulse train length=3 pulses, dead time=10 ms. $M_{az}$ was set to zero by the excitation pulse, and competing effects of RF saturation, chemical exchange, and relaxation influence the return to equilibrium. When saturation was applied, attenuation caused by the off-resonance RF saturation pulse train was observed during recovery ($B_1$=6 μT). The magnetization time course is dependent on the applied saturation pulse shape (Gaussian, Sinc3, Rectangular). The measurement of $S_0$ is given by the recovery of longitudinal magnetization in the absence of saturation ($B_1$=0 μT). The influence of discrete Gaussian and Sinc3 pulses could be seen reflected in a corresponding attenuation of $M_{az}$, while the rectangular pulses result in a more complicated perturbation of $M_{az}$.

The RF saturation was modeled with Gaussian RF pulses implemented in the Bloch-McConnell equations. The Gaussian pulses were implemented by dividing a truncated Gaussian waveform of a given duration (standard deviation approximately 20% of total duration, truncated at approximately 2.5 standard deviations) into a series of 101 short block pulses and applying these piecewise block pulses consecutively into the simulation. A Sinc3 pulse (truncated 3-lobed Sinc pulse) and rectangular (hard) RF pulse of constant amplitude were also implemented using the same approach. The RF saturation pulse trains consisted of a number of these pulses applied consecutively, with a "dead time" of 10 ms between pulses that is often necessary due to hardware limitations.

The longitudinal relaxation after water excitation was also modeled to estimate available longitudinal magnetization for subsequent acquisitions. For the CEST-EPI sequence shown in FIG. 1, one repetition consisted of a non-selective RF off-resonance saturation pulse train followed by readout of a single image slice. Because the RF pulse train is non-selective, this saturation was applied to all image slices after each repetition in the simulation. To model the relaxation occurring in the water pool during image acquisition (free-precession) and prior to the next off-resonance saturation pulse train, $$M_{az}(t_5) = M_{az0} - [M_{az0} - M_{az}(t_1)] * e^{-\frac{t_5-t_1}{T_{1a}}} \text{ and}$$

$$M_{bz}(t_5) = M_{bz0} - [M_{bz0} - M_{bz}(t_1)] * e^{-\frac{t_5-t_1}{T_{1b}}}$$

were applied between saturation pulse trains with $t_5-t_1$=60 ms (estimated for an echo time (TE)=27 ms during EPI readout) as well as during the short dead time periods (10 ms) between saturation pulses in the pulse train.

Exchange rate constants were also calculated. To determine the constants $k_0$ and $k_{base}$ for amino acid amines, a phantom of 12 solutions containing 50 mM glutamine dissolved in distilled water at varying pH (5.4 to 7.6 in units of 0.2) was constructed. Previous studies have shown that amine CEST contrast can be generated using RF pulses of short duration and high amplitude. The maximum Gaussian RF amplitude that can be repeatedly achieved on clinical scanners within hardware limitations was empirically determined to be approximately 6 μT, with Gaussian pulses being the default saturation pulse shape for most MT applications. Therefore, CEST-EPI data were acquired for the custom phantom on a Siemens 3 T Prisma system using a saturation pulse train of 3×100 ms Gaussian pulses of amplitude $B_1$=6 μT (TR=380 ms), with 51 spectral points acquired between −5.0 and 5.0 ppm. Glutamine samples were split into 2 groups of 6 samples, as only 6 samples could be scanned at a time. $MTR_{asym}$ at 3.0ppm was calculated for the solutions of different pH.

Nonlinear least squares regression was then used to estimate $k_0$ and $k_{base}$ using the simulation equations applied to phantom measurements (MATLAB; Mathworks, Inc., Natick, Mass.). For the simulation, $T_1$ and $T_2$ of bulk water ($T_{1a}$ and $T_{2a}$) were estimated as 3.375 s and 2.500 s, respectively. The $T_1$ and $T_2$ of the amine pool ($T_{1b}$ and $T_{2b}$) were estimated as 0.2 s and 0.1 s, respectively, based on estimates from the literature. After fitting, the resulting values of $k_0$ and $k_{base}$ were then used to calculate the amine exchange rate, $k_b$, for a specific pH. To verify the repeatability of $k_0$ and $k_{base}$ measurements and the accuracy of resulting simulations, the same pH phantom was scanned using a similar CEST-EPI sequence, but replacing the Gaussian saturation pulses with Sinc3 pulses. The previously measured values of $k_0$ and $k_{base}$ were used to generate the expected z-spectrum during application of and the respective acquisition parameters. Pearson's correlation coefficient was used to assess the association between the simulated and measured values of $MTR_{asym}$.

Simulations estimated $k_0$=75.9 Hz and $k_{base}$=5.64 Hz by fitting phantom data acquired using Gaussian saturation pulses ($R^2$=0.9853, Slope=0.9637±0.0241, P<0.0001). These values were then used to calculate the amine exchange rate $k_b$ from pH for the remainder of the simulations. These parameters were then used to forecast the z-spectrum using Sinc3 pulses. Results demonstrated a strong match between simulations and experimental data obtained using Sinc3 saturation pulses ($R^2$=0.9764, Slope=0.9849±0.0260, P<0.0001).

Figure 3A:
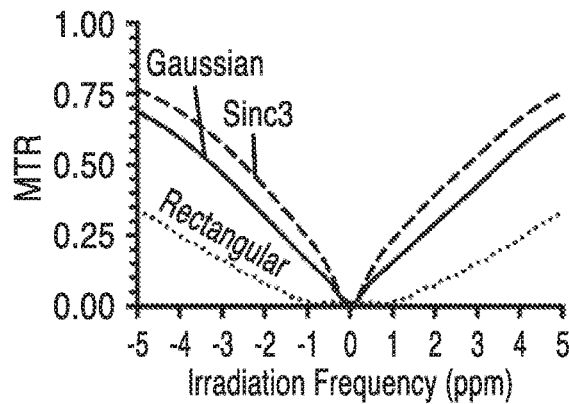
FIG. 3A is a graph depicting glutamine z-spectrum asymmetry, $MTR_{asym}$ (3.0 ppm), obtained from the z-spectrum of glutamine phantoms at various pH and concentrations. The $MTR_{asym}$ of the CEST z-spectrum showing increased asymmetry with decreasing pH at 3T.
Figure 3B:
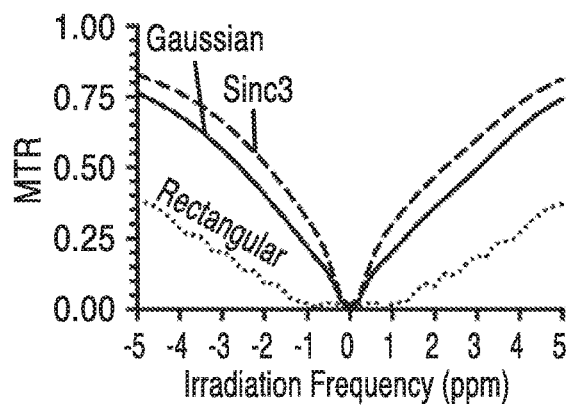
FIG. 3B is a graph depicting glutamine z-spectrum asymmetry, $MTR_{asym}$ (3.0 ppm), for different pH, concentration, and temperature.
Figure 3C:
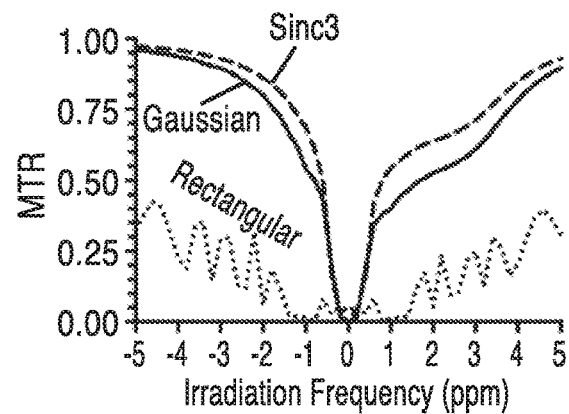
FIG. 3C is a graph depicting CEST z-spectrum asymmetry, $MTR_{asym}$ (3.0 ppm) for glutamine, glycine, and phenylalanine phantoms (100 mM) as a function for pH.

The simulated and experimental Z-spectra for different RF saturation pulse shapes were also evaluated as shown in FIG. 3A to FIG. 3C. The fidelity of the simulations was tested against phantom data for Gaussian, Sinc3 and rectangular pulses. Both simulations and experimental acquisitions used a saturation pulse train of 3×100 ms pulses with amplitude $B_1$=4 μT for Gaussian, Sinc3 and rectangular pulse shapes and a TR=380 ms applied to a phantom containing 50 mM glutamine at a pH of 6.0.

Glutamine z-spectrum asymmetry, $MTR_{asym}$ (3.0 ppm), obtained from the z-spectrum of glutamine phantoms at various pH and concentrations is shown in FIG. 3A. The MTR of the CEST z-spectrum showing increased asymmetry with decreasing pH at 3 T. FIG. 3B depicts glutamine z-spectrum asymmetry, $MTR_{asym}$ (3.0 ppm), for different pH, concentrations, and temperatures. FIG. 3C is a graph depicting CEST z-spectrum asymmetry, $MTR_{asym}$ (3.0 ppm) for glutamine, glycine, and phenylalanine phantoms (100 mM) as a function for pH.

The simulated and experimental z-spectra were directly compared for each pulse type to verify the correlation had an approximate slope of unity. The simulated estimates of the z-spectrum matched well with experimental data for Gaussian, Sinc3 and rectangular pulses at pH=6.0. Interestingly, rectangular saturation pulses showed oscillations in the z-spectra for both simulations and experimental data, along with increased overall attenuation over all frequencies compared with Gaussian and Sinc3 pulses.

Experimental measures of $MTR_{asym}$ also closely resembled the simulation data with Gaussian pulses providing slightly higher $MTR_{asym}$ at 3.0ppm compared with Sinc3 pulses. Linear correlation between simulated and measured $MTR_{asym}$ for Gaussian pulses ($R^2$=0.9793, Slope=1.014±0.0077, P<0.0001) and Sinc3 pulses ($R^2$=0.9909, Slope=1.005±0.0045, P<0.0001) were high and approximately unity. Rectangular pulses showed a substantially lower correlation coefficient, but still demonstrated a 1:1 relationship between simulated and measured values of MTR ($R^2$=0.7907, Slope=1.062±0.040, P<0.0001).

Results showed that the z-spectrum was highly dependent on saturation pulse shape, repetition time, saturation amplitude, magnetic field strength, and $T_2$ within bulk water.

However, the z-spectrum was only minimally influenced by saturation pulse duration and the specific relaxation rates of amine protons. The results suggested a Gaussian saturation pulse train consisting of 3×100 ms pulses using the minimum allowable repetition time is optimal for achieving >90% available contrast across all tissues.

EXAMPLE 2

The effects of saturation pulse shape, pulse duration, pulse train length, repetition times, and relaxation rates of bulk water and exchangeable amine protons on the CEST signal were also explored for normal-appearing white matter (NAWM), glioma, and cerebrospinal fluid.

The concentration of amino acids in normal neural tissues has been estimated around 20-25 mM. However, in addition to the standard proteinogenic amino acids, many amino acid derivative metabolites including norepinephrine, 5-hydroxytryptophan, levodopa and other neurotransmitters possess an amine functional group that will also contribute to the CEST signal at 3.0 ppm. Proteins such as bovine serum albumin (BSA) have also shown characteristics of a fast-exchanging amine component at 3.0 ppm, likely from common amine groups on exposed protein side chains. Thus, a total amine concentration of 50 mM was assumed in neural tissues and used for simulation purposes in normal-appearing white matter (NAWM) ($T_{1a}$=1.22 s, $T_{2a}$=0.107 s), tumor tissue ($T_{1a}$=1.37 s, $T_{2a}$=0.170 s) and cerebrospinal fluid (CSF) ($T_{1a}$=3.375 s, $T_{2a}$=2.500 s, similar to fluid phantoms). A $T_{1b}$ of 0.2 s and $T_{2b}$ of 0.1 s were used for the amine pool.

To demonstrate the effects of saturation pulse shape on the CEST effect in tissue, the application of a Gaussian, Sinc3, and rectangular pulse trains all consisting of 3×100 ms pulses of amplitude 6 µT (TR=380 ms) at pH=6.0 were simulated. MTR at spectral points between −5.0 and +5.0 ppm were calculated to obtain simulated z-spectra in these tissues.

Figure 4A:
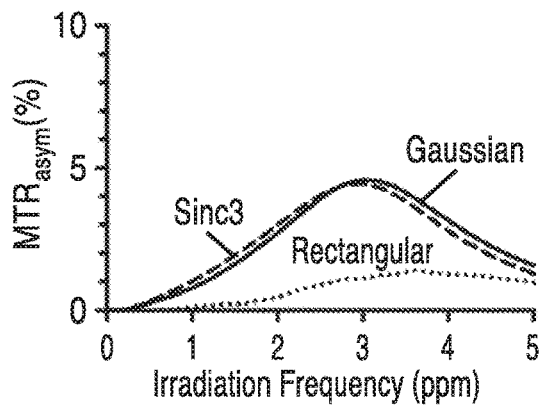
FIG. 4A is a graph of simulated z-spectra for a two-pool amine model in a normal-appearing white matter (NAWM) a CEST-EPI sequence with Gaussian, Sinc3, and Rectangular RF saturation pulses.
Figure 4B:
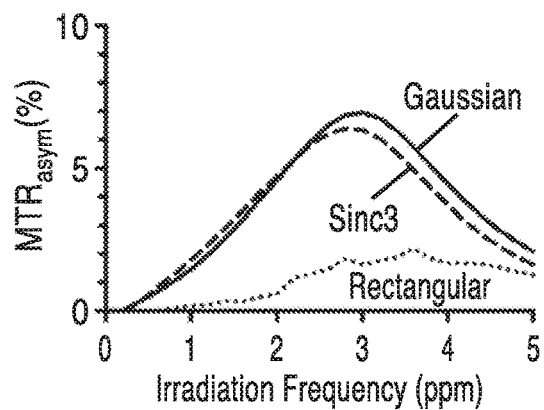
FIG. 4B is a graph of simulated z-spectra for a two-pool amine model in a glioma for the three different saturation pulse shapes.
Figure 4C:
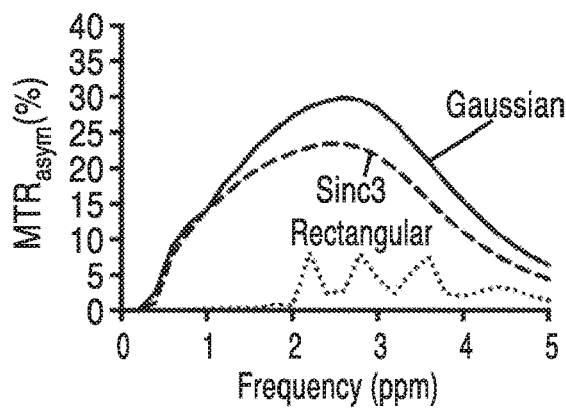
FIG. 4C is a graph of simulated z-spectra for a two-pool amine model in cerebral spinal fluid (CSF) for the three different saturation pulse shapes.
Figure 5A:
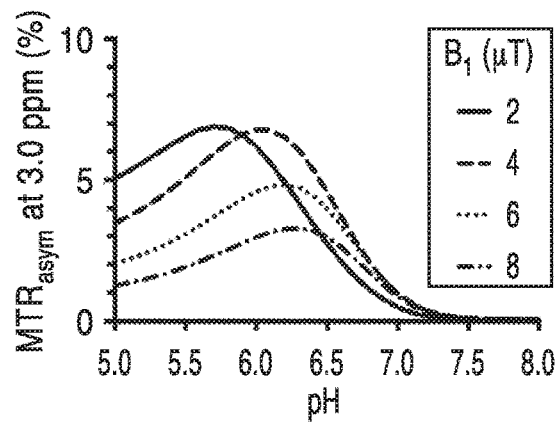
FIG. 5A through FIG. 5C are graphs of $MTR_{asym}$ for the data shown in FIGS. 4A, 4B and 4C, respectively. Gaussian and Sinc3 pulses appear to produce higher $MTR_{asym}$ at 3.0ppm compared with rectangular pulses.
Figure 5B:
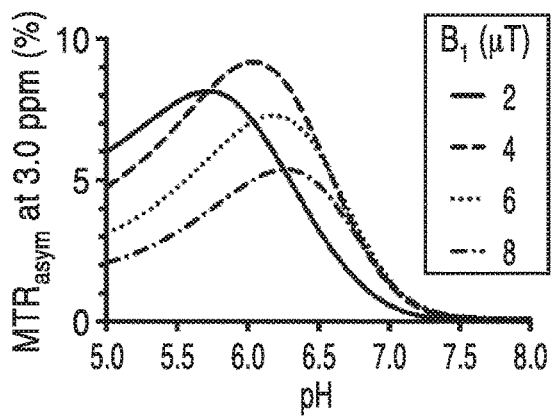
Figure 5C:
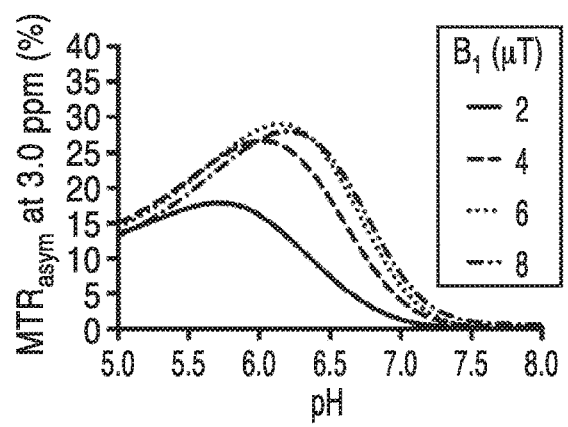

FIG. 4A is a graph of simulated z-spectra for a two-pool amine model in a normal-appearing white matter (NAWM) a CEST-EPI sequence with Gaussian, Sinc3, and Rectangular RF saturation pulses. FIG. 4B shows simulated z-spectra for a two-pool amine model in a glioma for the three different saturation pulse shapes, and, FIG. 4C shows simulated z-spectra for a two-pool amine model in cerebral spinal fluid (CSF) for the three different saturation pulse shapes. FIG. 5A through FIG. 5C are graphs of $MTR_{asym}$ for the data shown in FIGS. 4A, 4B and 4C, respectively.

In NAWM and tumor tissue, Gaussian and Sinc3 pulses produced less overall attenuation across all frequencies when compared with rectangular saturation. The z-spectra for NAWM and glioma showed more attenuation at all irradiation frequencies when compared with CSF. Gaussian and Sinc3 pulses showed higher $MTR_{asym}$ specific to the amine proton resonance frequency when compared with the rectangular pulse for both NAWM and glioma.

Saturation pulse lengths were also compared. Clinical scanners often have limitations on the RF pulse duration to limit SAR and local heating. The maximum pulse length achievable on the MR system was approximately 100 ms. However, it remains unclear whether pulse trains consisting of higher numbers of short pulses is preferable to a lower number of pulses with longer saturation duration.

To determine the dependence of $MTR_{asym}$ at 3.0 ppm on pH for different saturation pulse durations for NAWM, glioma and CSF, RF saturation pulses with a total saturation of approximately 300 ms per repetition were examined under 4 scenarios: A) 12×25 ms pulses; B) 6×50 ms pulses; C) 3×100 ms pulses; and D) 1×300 ms pulse. A dead time of 10 ms was used between all pulses. Because the additional dead times between shorter saturation pulses will lengthen the total pulse train time, $t_5$-$t_1$ was adjusted to keep an identical TR=470 ms and equivalent saturation time integral between simulations ($t_5$-$t_1$=60, 120, 150, and 170 ms, respectively).

Changes in saturation pulse length did not result in consequential differences in $MTR_{asym}$ at 3.0ppm in any of the three tissue types. In NAWM and glioma, $MTR_{asym}$ at 3.0ppm was higher for pulses of 100 ms. In CSF, $MTR_{asym}$ at 3.0ppm was higher when using 1×300 ms pulse. These results suggest saturation pulse trains using 100 ms pulses may be preferred for characterization of glioma tissues.

Next, the dependence of $MTR_{asym}$ at 3.0ppm on pH was evaluated for different repetition times (TR) using a constant saturation pulse train length to understand the effects of increasing longitudinal relaxation time between saturation pulse trains for NAWM, glioma and CSF. The minimum TR achievable on a 3 T Siemens Prisma for a pulse train of 3×100 ms Gaussian pulses is 380 ms ($t_1$-$t_0$=320 ms, $t_5$-$t_1$=60 ms). The TR was then varied between 380, 500, 1000, and 2000 ms while holding the pulse train length and all other parameters constant. The effect of the specific number of 100 ms pulses used in the pulse train was also examined for the minimum TR available. Pulse train lengths of 1, 2, 3, 5, and 25 pulses were used with minimum TRs of 160, 270, 380, 600, and 2580 ms, respectively.

Both glioma tissue and CSF showed decreased $MTR_{asym}$ at 3.0ppm with increasing TR, likely due to increased longitudinal relaxation occurring between periods of saturation. In NAWM, $MTR_{asym}$ at 3.0ppm increased only slightly with increasing TR and then decreased with further increases in TR. These results suggest the minimum allowable TR is preferred for highest $MTR_{asym}$ at 3.0ppm in glioma. This trend also remained for pulse train lengths of 1×100ms and 5×100ms.

The difference in $MTR_{asym}$ at 3.0 ppm for various pH was small when changing the saturation pulse train length and selecting the minimum allowable TR. However, in CSF, a longer pulse train resulted in higher $MTR_{asym}$ at 3.0 ppm. For pH between 6.0 and 7.0 in CSF, $MTR_{asym}$ at 3.0 ppm reached approximately 90% of maximum contrast available when using a pulse train length of 3. This suggests 3 pulses may be preferred for obtaining at least 90% of allowable pH-weighted contrast for all tissues of interest within the brain.

The effects of saturation pulse amplitude and scanner field strength were also evaluated. The dependence of $MTR_{asym}$ at 3.0 ppm on pH was then tested for various $B_1$ pulse amplitudes. A saturation pulse train consisting of 3×100 ms Gaussian pulses of amplitudes $B_1$=2, 4, 6, and 8 µT were used with a TR=380 ms. Additionally, the dependence of $MTR_{asym}$ at 3.0ppm on pH was also explored for various $B_0$ field strengths including 1.5, 3.0, 7.0, 9.4, and 11.0 T, again using a saturation pulse train of 3×100 ms Gaussian pulses of $B_1$=6 µT and TR=380 ms.

Figure 6A:
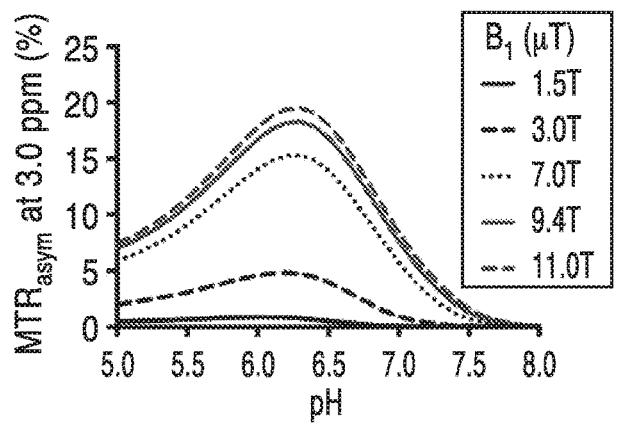
FIG. 6A is a graph of simulated $MTR_{asym}$ at 3.0ppm for various pH values and different $B_1$ amplitudes in NAWM.
Figure 6B:
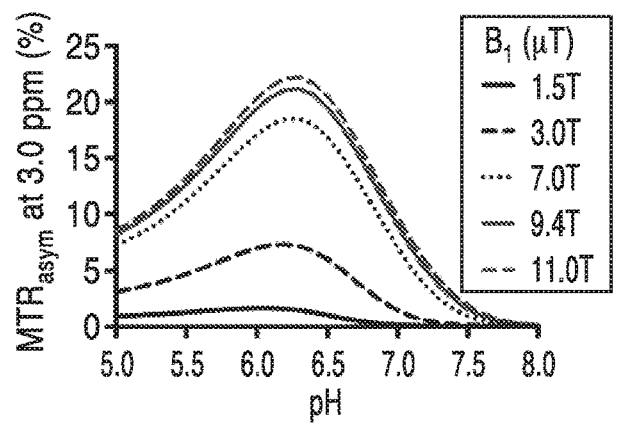
FIG. 6B is a graph of simulated $MTR_{asym}$ at 3.0ppm for various pH values and different $B_1$ amplitudes in glioma.
Figure 6C:
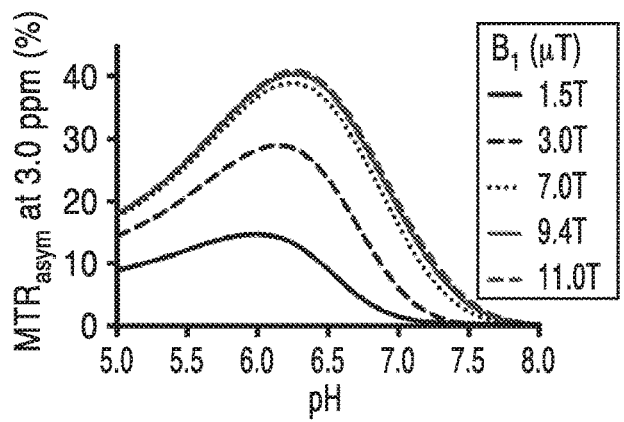
FIG. 6C is a graph of simulated $MTR_{asym}$ at 3.0ppm for various pH values and different $B_1$ amplitudes in CSF.
Figure 7A:
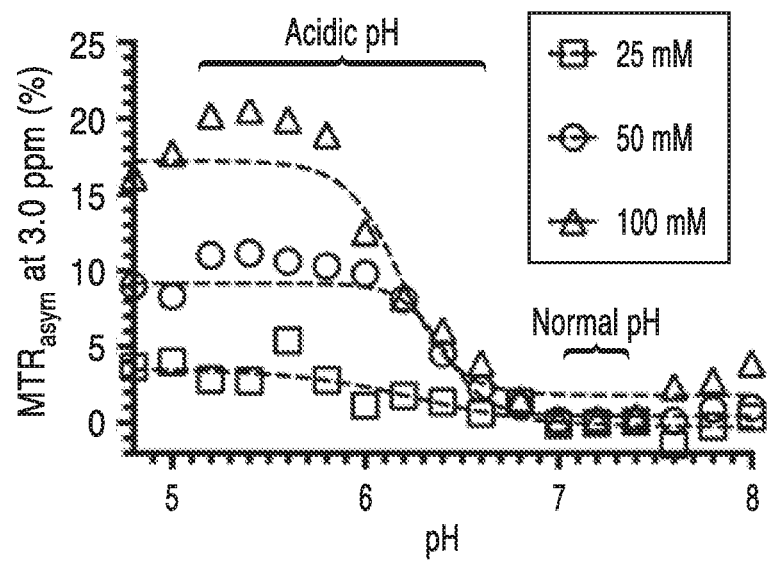
FIG. 7A is a graph of simulated $MTR_{asym}$ at 3.0ppm for various pH values in NAWM, at different $B_0$ field strengths.
Figure 7B:
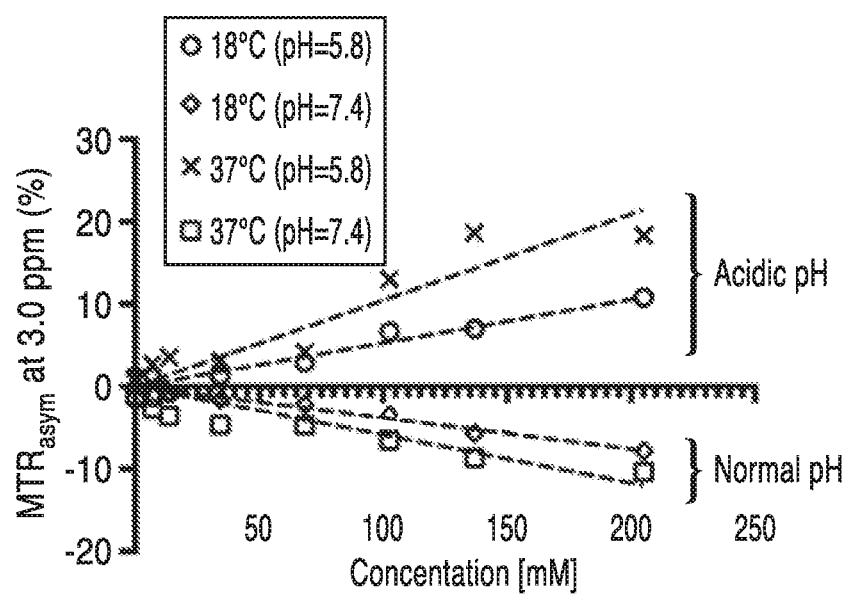
FIG. 7B is a graph of simulated $MTR_{asym}$ at 3.0ppm for various pH values in glioma at different $B_0$ field strengths.
Figure 7C:
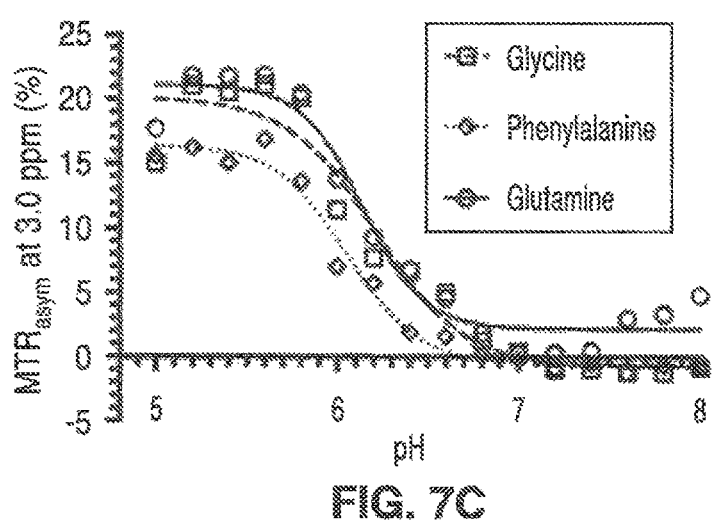
FIG. 7C is a graph of simulated $MTR_{asym}$ at 3.0ppm for various pH values in CSF at different $B_0$ field strengths.

Simulations of $MTR_{asym}$ at 3.0ppm for various pH values and different $B_1$ amplitudes in NAWM, glioma and CSF are shown in FIG. 6A through FIG. 6C. Simulations of $MTR_{asym}$ at 3.0 ppm for various pH values in NAWM, glioma and CSF at different $B_0$ field strengths are shown in FIG. 7A through FIG. 7C.

It was observed that higher $B_1$ amplitudes, in general, did not result in higher $MTR_{asym}$ at 3.0ppm for any of the tissues examined; however, there was a slight shift in the pH range with CEST sensitivity across different amplitudes (FIG. 6A to FIG. 6C). In tumor tissue, maximum $MTR_{asym}$ at pH<6.5 appeared to be maximized at 4 µT, although the resulting $MTR_{asym}$ were approximately equivalent for $B_1$=4 and 6 µT for pH>6.5 (FIG. 6B). In CSF, $MTR_{asym}$ was highest at high $B_1$ values of 6 and 8 µT (FIG. 6C).

$MTR_{asym}$ generally increased with increasing $B_0$ field strength, although the increase was not linear. The range of pH values exhibiting approximately linear sensitivity to $MTR_{asym}$ also shifted higher with increasing $B_0$ as seen in FIG. 7A to FIG. 7C. Together, this suggests amine CEST-EPI should be performed at high field strengths (≥7T) for maximum pH-weighted contrast, but field strengths as low as 3T can provide adequate sensitivity.

Lastly, the influence of relaxation rates for both bulk water and the labile proton pool on $MTR_{asym}$ at 3.0ppm for various pH were examined. NAWM relaxation rates were used as reference values. $T_{1a}$ was varied between 0.5 and 3 s, $T_{2a}$ was varied between 0.05 and 0.3 s, $T_{1b}$ was varied between 0.1 and 1 s, and $T_{2b}$ was varied between 0.01 and 0.5 s. A saturation pulse train of 3×100 ms Gaussian pulses of amplitude $B_1$=6 µT and TR=380 ms were used for simulation purposes.

It was seen that increasing $T_{1a}$ first increased and then decreased the maximum $MTR_{asym}$ at 3.0ppm within the tested range, likely due to competing effects of saturation at both the target frequency (+3.0ppm) and control frequency (−3.0ppm) used to calculate $MTR_{asym}$. Increases in $T_{2a}$ resulted in increased $MTR_{asym}$ at low pH. Varying the amine pool relaxation parameters $T_{1b}$ and $T_{2b}$ had a negligible effect on $MTR_{asym}$, suggesting pH-weighted CEST contrast is influenced greater by fluctuations in relaxation rate within the bulk water than the amine proton pools.

EXAMPLE 3

To further demonstrate the methods, clinical testing of fast pH-weighted imaging at 3T of patients with malignant glioma was performed. In this clinical evaluation, a total of 18 patients with histologically confirmed primary glioma were enrolled in clinical trial. All patients signed informed written consent to have pH-weighted CEST-EPI collected as part of their pre-operative MR examinations. Of these 18 patients, 4 had WHO grade II tumors of various histopathologies, 7 patients had anaplastic malignant gliomas with WHO III, and 7 patients had WHO IV glioblastoma. Patients were a mixture of both newly diagnosed and recurrent tumors.

All patients with recurrent disease (n=6) received 6-[$^{18}$F] fluoro-L-dopa Positrion Emission Tomography ($^{18}$F-FDOPA PET) scans to confirm the presence of metabolically active tumor. $^{18}$F-FDOPA PET scans were acquired using a high-resolution full-ring PET scanner (ECAT-HR; CTI/Mimvista).

All patients had anatomic, physiologic, and pH-weighted MRI on a 3T Siemens Prisma Fit (Siemens Medical; Erlangen, Germany). All patients received the international standardized MRI protocol consisting of dual echo proton-density/T2-weighted turbo spin echo images, diffusion tensor imaging (DTI), fluid-attenuated inversion recovery (FLAIR) images, and 1 mm isotropic parameter matched 3D inversion-recovery gradient recalled echo (IR-GRE) images before and after injection of 0.1 mmol/kg of Gd-DTPA.

The pH-weighted CEST-EPI scans were collected prior to contrast administration and consisted of the following scan parameters: field-of-view (FOV)=256×256 mm, matrix size=128×128, number of slices=25, slice thickness=4 mm with no interslice gap, TE/TR=27/9380 ms (total TR for all slices), bandwidth=1628 Hz, and generalized autocalibrating partially parallel acquisition (GRAPPA) factor=2. Off-resonance saturation was applied using a pulse train of 3×100 ms Gaussian pulses with amplitude of 6 µT, with spoiling gradients to remove transverse magnetization prior to each readout. A z-spectrum was acquired using off-resonance saturation frequencies of ±3.5, ±3.4, ±3.3, ±3.2, ±3.1, ±3.0, ±2.9, ±2.8, ±2.7, ±2.6, ±2.5, ±0.3, ±0.2, ±0.1, and 0.0 ppm. One scan with $B_1$=0 µT ($S_0$ image) was acquired for normalization. $B_0$ inhomogeneity correction was performed by finding the minimum signal intensity between ±0.3 ppm for each voxel and shifting that voxel's z-spectrum accordingly. An integral of spectral points between 2.8 and 3.2 ppm was then calculated for both positive and negative frequencies to obtain $S(\omega)$ and $S(-\omega)$. Total scan time for CEST-EPI was approximately 5 minutes. Since many of the low grade gliomas and anaplastic tumors contained significant non-enhancing disease, values of $MTR_{asym}$ within T2-hyperintense lesions representative of non-enhancing tumor were evaluated for these patients and compared across tumor grade.

All patients evaluated had regions of elevated $MTR_{asym}$ at 3.0ppm within $T_2$ hyperintense lesions, even without the presence of contrast enhancement or macroscopic necrosis. Post-contrast T1-weighted images, T2-weighted FLAIR images, $^{18}$F-FDOPA PET, and pH-weighted CEST-EPI estimates of $MTR_{asym}$ at 3.0 ppm for representative patients with WHO II, III, and IV tumors were obtained. In all patients, regions of elevated $^{18}$F-FDOPA uptake also showed elevated $MTR_{asym}$. However, some regions within the tumor illustrated elevated CEST contrast in regions with low to moderate $^{18}$F-FDOPA uptake, suggesting CEST-EPI might add additional value to other molecular imaging techniques. In general, patients with WHO II and III tumors had lower $MTR_{asym}$ at 3.0 ppm compared with recurrent and newly diagnosed glioblastoma. Results verified this observation, indicating $MTR_{asym}$ was significantly different across tumor grade (ANOVA, P=0.0192), with WHO II and III tumors showing significantly lower mean measurements (Tukey, P<0.05 for WHO II vs. IV and WHO II vs. IV). If combined, WHO II and III tumors were significantly lower than WHO IV tumors (t-test, P=0.0049). Although not significant due to the limited number of patients, a closer examination of the data appeared to suggest newly diagnosed tumors, particularly glioblastoma, may have higher $MTR_{asym}$ at 3.0 ppm compared with recurrent tumors of the same grade, suggesting recurrent tumors may have inherently lower acidity than untreated, newly diagnosed tumors.

Overall, these results demonstrate the feasibility of performing fast pH-weighted imaging using CEST-EPI for clinical evaluation of gliomas. The pH-weighted CEST contrast increased with increasing tumor grade, with glioblastoma showing significantly higher acidity compared with WHO II or III gliomas.

The results from this study provide theoretical and experimental validation that amine CEST-EPI can be used for fast pH-weighted imaging in gliomas at 3T. Simulation results closely matched experimental results under all conditions explored, suggesting the model accurately accounted for the chemical exchange between amine protons and the bulk water pool. The results further suggest 3×100 ms Gaussian saturation pulses with minimum TR and a $B_1$ amplitude ≥4 µT results in 90% of available pH-weighted contrast across all brain tissue types within a pathophysiological range of pH values (6.0-7.2) when using CEST-EPI acquisition. Although the maximum $MTR_{asym}$ at low pH (<6.5) was greater for 4 µT than 6 µT in all tissues, the pH sensitivity is equivalent for pH>6.5. Because the optimal saturation pulse amplitude appears to increase with increasing relaxation times, an amplitude of 6 µT may still be necessary for ensuring that acidic regions within edematous tissue or non-enhancing tumor with long relaxation times can still be identified. Using these recommended parameters, a total of 29 z-spectral images and one $S_0$ image with full brain coverage can be obtained in less than 5 minutes, which is clinically feasible and significantly shorter than standard gradient echo techniques with acquisition times of more than 10-15 minutes.

EXAMPLE 4

In order to further demonstrate the functionality of the methods, a series of preclinical pH-weighted MRI experiments at 7T in C57BL/6 mice (6-8 weeks of age) injected either with PBS (control) or GL261 glioma cells were conducted. One C57BL/6 mouse was injected with phosphate buffered saline (PBS; control) while 9 C57GL/6 mice were injected with $2 \times 10^6$ GL261 glioma cells and allowed to grow for 14 days. Mice were sedated with 1-3% isoflurane under $O_2/N_2$ flow and respiration was monitored. Mice were kept warm with water heated to 37° C. circulated using a TP500 water pump (Gaymar Solid State). All images were acquired on a 7T Bruker Biospec system with a custom-built 2.2-cm RF birdcage coil. Each mouse was scanned less than one hour. A series of anatomical images as well as pH-weighted MR images in these mice were collected. Pre- and post-contrast 3D T1-weighted anatomical images were collected using a 3D fast low flip angle acquisition (FLASH) technique. Prior to contrast administration, pH-weighted CEST images were collected using a 2D gradient echo acquisition technique. Total CEST scan time was 10.5 minutes.

Results showed avid contrast enhancement and significantly higher $MTR_{asym}$ (Paired t-test, P=0.0002; Mean $MTR_{asym}$ in tumor=6.3% vs. 3.6% in contralateral tissue) when evaluated at an irradiation frequency of 3.0ppm offset in tumor, which was not observed in the control animals. Histology confirmed the areas showing an acidic signature were composed of relatively hypercellular, highly necrotic tumor tissue.

EXAMPLE 5

To demonstrate that CEST contrast at 3.0ppm is elevated in human brain tumors under conditions where low pH is thought to occur, a series of high grade gliomas (WHO III-IV) using pH-weighted MRI, 6-[$^{18}$F] fluoro-L-dopa ($^{18}$F-FDOPA) PET and single-voxel MR spectroscopy were assessed. Results demonstrated a positive $MTR_{asym}$ on CEST at 3.0ppm in regions with elevated $^{18}$F-FDOPA PET uptake and elevated lactate concentration, implying that highly aggressive tumors with elevated amino acid uptake for fuel and increased lactic acid in solution from oncologic metabolism under hypoxic conditions will consistently generate an acidic tumor signature using CEST MRI at 3.0ppm.

A total of 25 patients with histologically confirmed primary gliomas (WHO II-IV) were enrolled in the clinical trial. A total of 3 patients received CEST imaging, single-voxel MR spectroscopy, and $^{18}$F-FDOPA PET imaging within 1 month for direct comparison, 2 patients received stereotactic pH-image-guided biopsies (a suspected low-grade glioma and a suspected recurrent glioblastoma), and 20 patients with histologically confirmed glioblastoma were evaluated at 3 time points: 1) Baseline—post-surgical and prior to radiochemotherapy; 2) Mid-Treatment—approximately 3 weeks after the start of radiochemotherapy; and 3) Post-Treatment —approximately 6-10 weeks after the start of radiochemotherapy, or 0-4 weeks after completion of concurrent radiation and chemotherapy. All glioblastoma patients evaluated underwent maximal surgical resection followed by standard treatment with radiotherapy and concurrent temozolomide.

A total of 1 to 5 slices of CEST images with varying z-spectral points ranging from 5 to 51 and ranging from −5.0 ppm to +5.0 ppm were acquired in clinical patients. A radiofrequency saturation pulse train of 3, 100 ms pulses (50% duty cycle) at $B_1$=6.0 µT were applied, followed by a 70° excitation pulse and GRE readout. For biopsy patients, three slices were acquired through the largest extent of the tumor using spectral points acquired at 0, ±0.125, ±0.25, ±0.375, ±0.5, ±2.5, ±2.75, ±3.0, ±3.25, and ±3.5 ppm, rather than a full z-spectrum with a single slice.

To confirm that regions suspected of containing acidic tissue on pH-weighted MRI contained viable tumor, pH-weighted MR-guided biopsies were preformed in two patients. The first case consisted of a 26-year-old male patient with a large area of $T_2$ hyperintensity, suggestive of tumor, but no contrast enhancement. $^{18}$F-FDOPA PET, perfusion MRI, and diffusion MRI were also negative. PH-weighted MRI showed an acidic signature consistent with tumor on inferior aspects, whereas superior regions did not demonstrate this signature.

To test whether an acidic microenvironment increases resistance to radiation and chemotherapies in human brain tumors, pH-weighted imaging before, during, and after radiation therapy and temozolomide in twenty patients with newly diagnosed glioblastoma was performed and examined differences in progression-free survival (PFS). Patients with tumors that were acidic at baseline following surgical resection but prior to radiation and temozolomide, defined by a significant region (>50%) of positive CEST asymmetry at 3.0 ppm within areas of contrast enhancement and/or $T_2$ or FLAIR hyperintensity, demonstrated a significantly longer PFS compared with patients lacking significantly acidic tumors (Log-rank, P<0.0001; Median PFS for acidic tumors vs. non-acidic tumors=125 days vs. 450 days). Areas with low pH at baseline often forecasted regions of subsequent tumor growth on contrast-enhanced MRI.

The use of amine CEST-EPI for pH-weighted imaging in glioma patients showed elevated $MTR_{asym}$ at 3.0ppm in both enhancing and non-enhancing regions. Patients with glioblastoma (WHO-IV) had significantly higher $MTR_{asym}$ at 3.0ppm compared with lower grade gliomas (WHO-II and III), consistent with the hypothesis that more malignant tumors have more acidity, potentially due to increased tumor hypoxia from altered vascularity. Accordingly, CEST imaging of the amine protons on glutamine or other amino acid molecules can be used as a non-invasive pH-weighted MRI technique for human and preclinical investigation of malignant gliomas.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. A method for obtaining a magnetic resonance image or spectrum, the method comprising: (a) applying a radiofrequency saturation pulse train with a frequency off-resonance from bulk water; (b) applying an excitation pulse; (c) applying an imaging readout pulse train; and (d) producing an image from acquired image data, with one full image acquired at a range of frequency offsets.

2. The method of any preceding embodiment, further comprising: applying a spoiler gradient between the saturation pulse and the excitation pulse.

3. The method of any preceding embodiment, further comprising: motion correcting acquired image data; and correcting acquired data for $B_0$ inhomogeneity.

4. The method of any preceding embodiment, wherein said excitation pulse comprises a 1-2-1 water-only RF excitation pulse employed to avoid influence of chemical shift from fat protons.

5. The method of any preceding embodiment, wherein said images are acquired at off-resonance saturation frequencies of +/−0, 0.1, 0.2, 0.3, 2.5, 2.6, 2.7, 2.8, 2.9, 3.0, 3.1, 3.2, 3.3, 3.4, and 3.5 ppm.

6. The method of any preceding embodiment, wherein said saturation pulse train comprises three 100 ms Gaussian pulses at a high amplitude of at least 6 µT.

7. The method of any preceding embodiment, wherein said saturation pulse train comprises three 100 ms Sinc3 pulses.

8. The method of any preceding embodiment, wherein said imaging takes place in magnetic field strengths of 3T or greater in order to produce adequate contrast for the range of pH values commonly observed in cancer tissues.

9. The method of any preceding embodiment, wherein said readout is a readout selected from the group consisting of a Single shot EPI readout, a Multi-shot EPI readout and Gradient Echo readout.

10. A system for performing pH-weighted chemical exchange saturation transfer (CEST) magnetic resonance imaging (MRI), comprising: (a) a magnetic resonance imaging scanner adapted to image a subject; (b) an imaging controller with a computer processor coupled to the imaging scanner; and (c) a non-transitory computer-readable memory storing instructions executable by the computer processor; (d) wherein said instructions, when executed by the computer processor, perform steps comprising: (i) applying radiofrequency saturation pulse trains at a range of frequency offsets with frequencies off-resonance from bulk water; (ii) applying excitation pulses; (iii) applying imaging readout pulses; and (iv) acquiring image data and producing images from the acquired image data; and (e) a display configured to display the produced images.

11. The system of any preceding embodiment, wherein said instructions when executed by the computer processor further perform steps comprising: applying a spoiler gradient between the saturation pulse and the excitation pulse.

12. The system of any preceding embodiment, wherein said instructions when executed by the computer processor further perform steps comprising: motion correcting acquired image data; and correcting acquired data for $B_0$ inhomogeneity.

13. The system of any preceding embodiment, wherein said instructions when executed by the computer processor further perform steps comprising: obtaining a reference $S_0$ image; and calculating asymmetry around 2.8-3.2 ppm for each image voxel using the signal intensity of the $S_0$ image.

14. The system of any preceding embodiment, wherein said excitation pulse comprises a 1-2-1 water-only RF excitation pulse employed to avoid influence of chemical shift from fat protons.

15. The system of any preceding embodiment, wherein said saturation pulse train comprises three 100 ms Gaussian pulses at a high amplitude of at least 6 µT.

16. The system of any preceding embodiment, wherein said saturation pulse train comprises three 100 ms Sinc3 pulses.

17. The system of any preceding embodiment, wherein said readout is a readout selected from the group consisting of a Single shot EPI readout, a Multi-shot EPI readout and Gradient Echo readout.

18. A method for obtaining a magnetic resonance image or spectrum, the method comprising: (a) applying a radiofrequency saturation pulse train of three 100-ms pulses with a frequency off-resonance from bulk water; (b) applying a spoiler gradient; (c) applying a 1-2-1 water-only RF excitation pulse; (d) applying an echo planar imaging readout pulse train; and (e) producing an image from acquired image data, with one full image acquired at a range of frequency offsets.

19. The method of any preceding embodiment, wherein said saturation pulse train comprises a pulse selected from the group of pulses consisting of a Sinc3 pulse, a rectangular pulse and a Gaussian pulse at a high amplitude of at least 6 µT.

20. The method of any preceding embodiment, wherein said echo planar imaging readout is a Single shot EPI readout or a Multi-shot EPI readout.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for obtaining a magnetic resonance image or spectrum, the method comprising:
   (a) applying a radiofrequency saturation pulse train with a frequency off-resonance from bulk water;
   (b) applying an excitation pulse;
   (c) applying an imaging readout pulse train; and
   (d) producing an image from acquired image data, with one full image acquired at a range of frequency offsets;
   wherein said saturation pulse train comprises three 100 ms Gaussian pulses at a high amplitude of at least 6 µT.

2. The method of claim 1, further comprising:
   applying a spoiler gradient between the saturation pulse and the excitation pulse.

3. The method of claim 1, further comprising:
   motion correcting acquired image data; and
   correcting acquired data for BO inhomogeneity.

4. The method of claim 1, wherein said excitation pulse comprises a 1-2-1 water-only RF excitation pulse employed to avoid influence of chemical shift from fat protons.

5. The method of claim 1, wherein said images are acquired at off-resonance saturation frequencies of +/−0, 0.1, 0.2, 0.3, 2.5, 2.6, 2.7, 2.8, 2.9, 3.0, 3.1, 3.2, 3.3, 3.4, and 3.5 ppm.

6. The method of claim 1, wherein said imaging takes place in magnetic field strengths of 3 T or greater in order to produce adequate contrast for the range of pH values commonly observed in cancer tissues.

7. The method of claim 1, wherein said readout is a readout selected from the group consisting of a Single shot EPI readout, a Multi-shot EPI readout and Gradient Echo readout.

8. A system for performing pH-weighted chemical exchange saturation transfer (CEST) magnetic resonance imaging (MRI), comprising:
   (a) a magnetic resonance imaging scanner adapted to image a subject;
   (b) an imaging controller with a computer processor coupled to the imaging scanner; and
   (c) a non-transitory computer-readable memory storing instructions executable by the computer processor;
   (d) wherein said instructions, when executed by the computer processor, perform steps comprising:
     (i) applying radiofrequency saturation pulse trains at a range of frequency offsets with frequencies off-resonance from bulk water, wherein said saturation pulse train comprises three 100 ms Gaussian pulses at a high amplitude of at least 6 µT;
     (ii) applying excitation pulses;
     (iii) applying imaging readout pulses; and
     (iv) acquiring image data and producing images from the acquired image data; and
   (e) a display configured to display the produced images.

9. The system of claim 8, wherein said instructions when executed by the computer processor further perform steps comprising:
   applying a spoiler gradient between the saturation pulse and the excitation pulse.

10. The system of claim 8, wherein said instructions when executed by the computer processor further perform steps comprising:
   motion correcting acquired image data; and
   correcting acquired data for BO inhomogeneity.

11. The system of claim 8, wherein said instructions when executed by the computer processor further perform steps comprising:
   obtaining a reference $S_0$ image; and
   calculating asymmetry around 2.8-3.2 ppm for each image voxel using the signal intensity of the $S_0$ image.

12. The system of claim 8, wherein said excitation pulse comprises a 1-2-1 water-only RF excitation pulse employed to avoid influence of chemical shift from fat protons.

13. The system of claim 8, wherein said readout is a readout selected from the group consisting of a Single shot EPI readout, a Multi-shot EPI readout and Gradient Echo readout.

14. A method for obtaining a magnetic resonance image or spectrum, the method comprising:

(a) applying a radiofrequency saturation pulse train of three 100-ms pulses with a frequency off-resonance from bulk water, wherein said saturation pulse train comprises three 100 ms Gaussian pulses at a high amplitude of at least 6 µT;
(b) applying a spoiler gradient;
(c) applying a 1-2-1 water-only RF excitation pulse;
(d) applying an echo planar imaging readout pulse train; and
(e) producing an image from acquired image data, with one full image acquired at a range of frequency offsets.

15. The method of claim 14, wherein said echo planar imaging readout is a Single shot EPI readout of a Multi-shot EPI readout.

* * * * *